US012560618B2

(12) United States Patent
Keane et al.

(10) Patent No.: US 12,560,618 B2
(45) Date of Patent: Feb. 24, 2026

(54) INNATE IMMUNE PROTEINS AS BIOMARKERS FOR CNS INJURY

(71) Applicant: UNIVERSITY OF MIAMI, Miami, FL (US)

(72) Inventors: Robert W. Keane, Miami, FL (US); W. Dalton Dietrich, Miami, FL (US); Juan Pablo De Rivero Vaccari, Miami, FL (US); Stephanie Adamczak, Miami, FL (US); M. Ross Bullock, Miami, FL (US); Allan Levi, Miami, FL (US); Michael Y. Wang, Miami, FL (US)

(73) Assignee: University of Miami, Miami, FL (US)

( * ) Notice: Subject to any disclaimer, the term of this patent is extended or adjusted under 35 U.S.C. 154(b) by 26 days.

(21) Appl. No.: 18/347,108

(22) Filed: Jul. 5, 2023

(65) Prior Publication Data

US 2023/0349929 A1     Nov. 2, 2023

Related U.S. Application Data

(63) Continuation of application No. 16/986,904, filed on Aug. 6, 2020, now abandoned, which is a continuation of application No. 15/214,868, filed on Jul. 20, 2016, now abandoned, which is a continuation of application No. 14/376,383, filed as application No. PCT/US2013/024941 on Feb. 6, 2013, now abandoned.

(60) Provisional application No. 61/595,254, filed on Feb. 6, 2012.

(51) Int. Cl.
| | |
|---|---|
| *G01N 33/68* | (2006.01) |
| *A61F 7/00* | (2006.01) |

(52) U.S. Cl.
CPC .......... *G01N 33/6896* (2013.01); *A61F 7/00* (2013.01); *G01N 2800/28* (2013.01); *G01N 2800/52* (2013.01); *G01N 2800/7095* (2013.01)

(58) Field of Classification Search
CPC ....... G01N 33/6896; G01N 2800/7095; G01N 2800/28; G01N 2800/52; A61F 7/00
See application file for complete search history.

*Primary Examiner* — Olga N Chernyshev
(74) *Attorney, Agent, or Firm* — Ted Whitlock

(57)     ABSTRACT

The present invention provides novel markers of the severity of a central nervous system injury, such as spinal cord injury or traumatic brain injury, in a patient. In particular, protein components of inflammasomes in the cerebrospinal fluid that can be used to assess the severity of central nervous system injury in a patient are disclosed. Methods of using such protein biomarkers to determine a prognosis, direct treatment and rehabilitation efforts, and monitor response to treatment for a patient with a central nervous system injury are also described.

18 Claims, 6 Drawing Sheets

Specification includes a Sequence Listing.

INNATE IMMUNE PROTEINS AS BIOMARKERS FOR CNS INJURY

CROSS-REFERENCE TO RELATED APPLICATIONS

This application is a continuation of U.S. patent application Ser. No. 16/986,904, filed Aug. 6, 2020, which is a continuation of U.S. patent application Ser. No. 15/214,868, filed Jul. 20, 2016, which is a continuation of U.S. patent application Ser. No. 14/376,383, filed Aug. 1, 2014, which is a national phase of International Application No. PCT/US2013/024941, filed Feb. 6, 2013, which claims priority to U.S. Provisional Application No. 61/595,254, filed Feb. 6, 2012, each of which is hereby incorporated by reference in its entirety.

DESCRIPTION OF THE TEXT FILE SUBMITTED ELECTRONICALLY

The Sequence Listing associated with this application is provided electronically in XML file format and is hereby incorporated by reference into the specification. The name of the XML file containing the Sequence Listing is UNMI 001 04US_SeqList_ST26.xml. The XML file is 4,528 bytes, was created on Jul. 4, 2023, and is being submitted electronically via the USPTO Patent Center.

FIELD OF THE INVENTION

The present invention relates generally to the fields of neurology, immunology, and diagnostics. In particular, the present invention relates to the identification of biomarkers in biological samples which can predict the severity of neuronal injury, such as spinal cord and traumatic brain injury, in patients. The identified biomarkers may also be used in determining prognosis, directing therapeutic and rehabilitation efforts, and monitoring response to treatment for patients with a central nervous system injury.

BACKGROUND OF THE INVENTION

Nucleotide-binding oligomerization domain (NOD)-containing protein-like receptors (NLRs) are a recently discovered class of innate immune receptors that play a crucial role in initiating inflammatory responses following tissue injury in the central nervous system (CNS) (Abulafia et al., 2009, Silverman et al., 2009). Previous work shows that NLRP1 (also known as NAcht leucine-rich-repeat protein 1 (NALP-1)) forms an inflammasome complex comprising NLRP1, the adaptor protein apoptosis-associated speck-like protein containing a caspase recruitment domain (ASC) and the caspase-1 enzyme that orchestrate the early inflammatory processes after spinal cord injury (SCI) and traumatic brain injury (TBI) via IL-1β activation (de Rivero Vaccari et al., 2008; 2009). The formation of inflammasomes is induced by physical damage to the plasma membrane, and by certain endogenous ligands referred to as danger associated molecular patterns (DAMPs) or exogenous ligands known as pathogen associated molecular patterns (PAMPs) (Bianchi, 2007, Wakefield et al., 2010). However, the full IL-1β response also depends on the activation of Toll-like receptors (TLRs) and/or purinergic ATP-gated receptors, which induce the transcription of pro-IL-1β.

Hyperinflammatory responses associated with tissue damage can promote pathogenesis of SCI and TBI via overproduction of IL-1β and other potentially neurotoxic products.

Inflammasome-mediated IL-1β overproduction is involved in the pathogenesis of type 2 diabetes, liver damage and muscular dystrophy (Kufer and Sansonetti, 2011). Moreover, increasing genetic evidence suggests that inflammasome activation could also drive adaptive immunity in types of dermatitis, skin related allergies and asthma (Kufer and Sansonetti, 2011). In addition, inflammasome components may be secreted into the extracellular milieu via a mechanism involving the exosome pathway (Bianchi, 2007). The inflammasome therefore has a complex connection with the control of adaptive immune responses that has become the subject of intense investigation. Whether inflammasomes are associated with tissue destructive inflammatory processes after SCI and TBI in humans has not been investigated.

TBI affects an estimated 1.5 million people each year and causes one-third of injury-related deaths. Approximately 5.3 million Americans are living today with a permanent TBI-related disability. Predicting the severity and outcome of TBI and well as SCI is difficult, given the lack of objective, laboratory-based biomarkers. Currently, the Glasgow Coma Scale (GCS) score (Teasdale et al., 1974) is the best available clinical predictor of injury severity; however, its value is limited in patients undergoing pharmacological paralysis for intubation, as a motor score cannot be obtained (Brain Trauma Foundation, American Association of Neurological Surgeons, 2000). Predicting outcome is further complicated by the heterogeneity of pathology in patients with a similar GCS score. Therefore, the identification of diagnostic and prognostic biomarkers that directly reflect injury to CNS cells is imperative. Such biomarkers of TBI and SCI will enable clinicians to assess the degree of damage to the brain or spinal cord, relay prognostic information to the patient's family members, and target acute and chronic treatments to specific CNS damage mechanisms. Therefore, an early, accurate diagnostic test designed to target neuroprotective strategies would be a most desirable prognostic tool.

Although, significant progress has been made regarding the verification and testing of various biomarkers after stroke and TBI, limited data are available regarding what biomarkers are appropriate for SCI. The biomarkers S-100β, neuron-specific enolase, neurofilament light chain and glial fibrillary acidic protein are significantly increased in cases of SCI in experimental animals studies (Skouen et al., 1999, Ma et al., 2001, Nagy et al., 2002, Cornefjord et al., 2004, Loy et al., 2005, Cao et al., 2008, Pouw et al., 2009). Although some biomarkers show promising results, these do not yet provide a sensitive prognostic tool. Quantitative standards for determining the extent of SCI and TBI during the acute phase must be developed and validated.

A new approach for evaluating the primary cord and brain damage in the acute phase is the assessment of biomarkers in the cerebrospinal fluid (CSF). Since CSF surrounds the spinal cord and brain, damage to the cord or brain may lead to the release of proteins and molecules from central nervous system cells into the CSF that may serve as biomarkers for SCI and TBI in the CSF. Several studies have been conducted concerning S-100β, neuron-specific enolase, neurofilament light chain, and glial fibrillary acidic protein (GFAP) in CSF and serum of animal models of SCI (Pouw et al., 2009). However, only one study has investigated neurofilament protein and GFAP in CSF after SCI in humans (Guez et al., 2003). Thus, there is a need in the art to identify biomarkers of neuronal damage following central nervous system injury in humans that can be used to ascertain the severity of the injury and facilitate the selection of an appropriate therapeutic strategy to maximize recovery.

SUMMARY OF THE INVENTION

The present invention is based, in part, on the discovery that NLRP1 (NALP-1) inflammasome components are secreted into the cerebrospinal fluid (CSF) acutely after SCI and traumatic brain injury (TBI) in humans. Elevated inflammasome protein levels in the CSF following central nervous system (CNS) injury represent the degree of neuroinflammation in CNS tissue and reflect the extent of inflammatory-induced damage. The CSF levels of inflammasome protein following injury correlate with the degree of functional recovery in patients and thus, can be used as acute biomarkers to predict patient prognosis and direct therapeutic interventions. Accordingly, the present invention provides a method of assessing the severity of a CNS injury in a patient.

In one embodiment, the invention provides a method of evaluating a patient suspected of having a CNS injury comprising providing a biological sample from a patient presenting with clinical symptoms consistent with a CNS injury, measuring the level of at least one inflammasome protein in the biological sample, determining the presence or absence of a protein signature associated with a CNS injury or a more severe CNS injury, wherein the protein signature comprises an elevated level of said at least one inflammasome protein, and selecting patients exhibiting the presence of the protein signature as having a CNS injury or a more severe CNS injury. In certain embodiments, said one or more inflammasome proteins are NLRP1 (NALP-1), ASC, or caspase-1. The diagnostic methods of the invention may further comprise administering a neuroprotective treatment to the patient based on the measured level of one or more inflammasome proteins, and following changes in the level of one or more inflammasome proteins as a mechanism to monitor response to treatment.

In some embodiments, the levels of one or more inflammasome proteins in the patient's sample can be used to prepare an inflammasome protein profile associated with CNS injury. The levels of inflammasome proteins in the profile may be determined relative to levels of the proteins in control samples or pre-determined reference values or ranges of reference values. The inflammasome protein profiles are, in some embodiments, indicative of the presence or severity of CNS injury in a patient. When such protein profiles are prepared from samples obtained from patients following administration of a neuroprotective treatment, the inflammasome protein profiles are indicative of therapeutic efficacy of the neuroprotective treatment in the patient.

The present invention also provides a method of determining a prognosis for a patient with a central nervous system injury. In one embodiment, the method comprises providing a biological sample, such as cerebrospinal fluid, obtained from the patient shortly after injury (e.g., within a week of injury), and measuring the level of at least one inflammasome protein in the biological sample to prepare an inflammasome protein profile, wherein the inflammasome protein profile is indicative of the prognosis of the patient. In particular embodiments, an elevated level of at least one inflammasome protein relative to a pre-determined reference value or range of reference values is indicative of a poorer prognosis or unfavorable patient outcome. For, example elevated inflammasome protein levels are predictive of the patient having a Glasgow Outcome Scale (GOS) score of 1 to 3 upon follow-up assessment. In other embodiments, a reduced level of at least one inflammasome protein relative to a pre-determined reference value or range of reference values is predictive of a favorable patient outcome (e.g., GOS score of 4 or 5 upon follow-up assessment). In certain embodiments, the method provides a prognosis for a patient with a spinal cord or traumatic brain injury.

The present invention also includes kits for preparing an inflammasome protein profile associated with CNS injury. In one embodiment, the kit comprises a labeled-binding partner, such as labeled-antibody or fragment thereof, that specifically binds to one or more inflammasome proteins, wherein said one or more inflammasome proteins are selected from the group consisting of NLRP1, ASC, caspase-1, and combinations thereof.

DETAILED DESCRIPTION OF THE INVENTION

Figure 1:
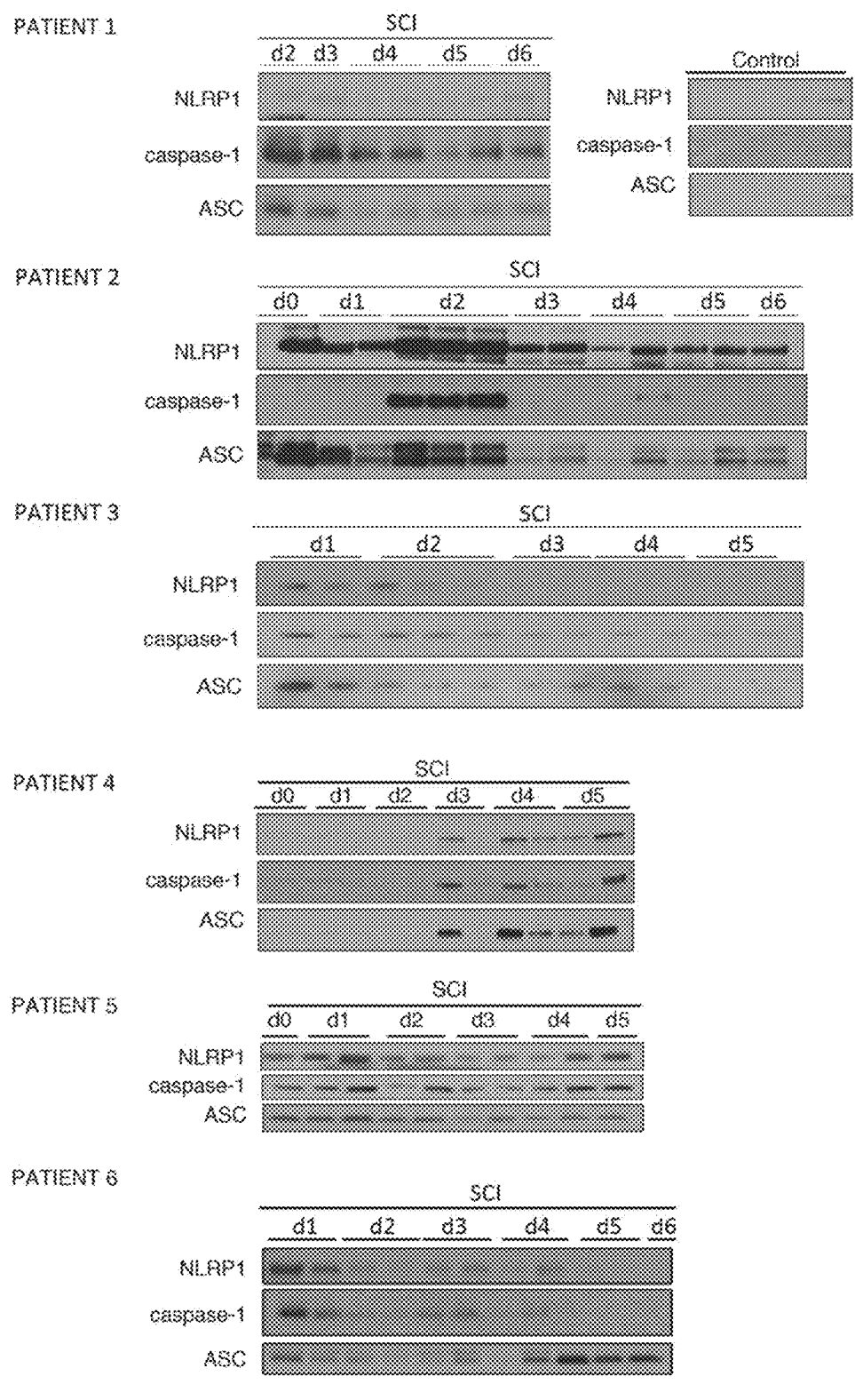
FIG. 1. NLRP1, ASC, and Caspase-1 are biomarkers that predict outcome after SCI. CSF samples were immunoblotted with antibodies against NLRP1, caspase-1 and ASC. CSF samples from uninjured patients were used as controls. Immunoblot analysis of 6 different cases of patients with SCI indicates that patients (2, 3 and 4) who express low levels of caspase-1 acutely after SCI have a better prognosis than subjects (1, 5 and 6) who have elevated levels of this protein in CSF.

The present invention is based, in part, on the discovery that NLRP1 inflammasomes play an important role in inflammatory responses after SCI and TBI in humans. In particular, the present inventors have surprisingly found that nucleotide-binding leucine-rich repeat pyrin domain containing protein 1 (NLRP1), the adaptor protein apoptosis-associated speck-like protein containing a caspase recruitment domain (ASC), and caspase-1 are secreted into the cerebrospinal fluid (CSF) of human patients following SCI and TBI. Thus, these inflammasome proteins represent sensitive biomarkers of the severity of central nervous system injury in human patients. Accordingly, the present invention provides a method of assessing the severity of a central nervous system injury in a patient by measuring the level of at least one inflammasome protein in a biological sample obtained from the patient, wherein the measured level of said at least one inflammasome protein is indicative of the severity of the central nervous system injury in the patient.

As used herein, the term "inflammasome" refers to a multi-protein complex that activates caspase-1 activity, which in turn regulates IL-1β, IL-18 and IL-33 processing and activation. See Arend et al. 2008; Li et al. 2008; and Martinon et al. 2002, each of which is incorporated by reference in their entireties. An "inflammasome protein" is a protein component of inflammasome complexes and can include, but is not limited to, an nucleotide binding domain, leucine-rich repeat containing (NLR) family member (e.g. NLRP1), ASC, caspase-1, caspase-11, X-linked inhibitor of apoptosis protein (XIAP), and pannexin-1. NLRP1 is also known as NAcht leucine-rich-repeat protein 1 (NALP-1). Thus, the terms "NLRP1" and "NALP-1 are used interchangeably throughout the disclosure. In certain embodiments, the method comprises measuring an inflammasome protein selected from the group consisting of NLRP1 (NALP-1), ASC, caspase-1, or combinations thereof. In one embodiment, the p20 subunit of active caspase-1 is measured.

The terms "patient" or "subject" are used interchangeably herein, and is meant a mammalian subject to be treated, with human patients being preferred. In certain embodiments, the patient is a pediatric patient. Pediatric patients include newborns (birth to 1 month of age), infants (1 month to 2 years of age), children (2 to 12 years of age), and adolescents (12-21 years of age). In some cases, the methods of the invention find use in experimental animals, in veterinary application, and in the development of animal models for disease, including, but not limited to, rodents including mice, rats, and hamsters, and primates.

In certain embodiments, the present invention provides a method of evaluating a patient suspected of having a central nervous system (CNS) injury. In one embodiment, the method comprises providing a biological sample from a patient presenting with clinical symptoms consistent with a CNS injury; measuring the level of at least one inflammasome protein in the biological sample; determining the presence or absence of a protein signature associated with a CNS injury or a more severe CNS injury, wherein the protein signature comprises an elevated level of said at least one inflammasome protein; and selecting patients exhibiting the presence of the protein signature as having a CNS injury or a more severe CNS injury.

A patient may be suspected of having a CNS injury on the basis of neurologic symptoms (motor, sensory, cognitive) and/or radiological evaluation (MRI, CT scan, X-ray) consistent with a CNS injury, e.g., after a physician's exam. In some embodiments, a patient suspected of having a CNS injury, particularly a spinal cord injury, may having a rating of A or B on the American Spinal Cord Injury Association (ASIA) Impairment Scale. The ASIA Impairment Scale is a standard diagnostic tool that assess a patient's motor and sensory function. The classification ratings and accompanying descriptions of the ASIA Impairment Scale are as follows:

| Classification/ Rating | Description |
| --- | --- |
| A | Complete: no motor or sensory function is preserved below the level of injury, including the sacral segments S4-S5 |
| B | Incomplete: sensory, but not motor, function is preserved below the neurologic level and some sensation in the sacral segments S4-S5 |
| C | Incomplete: motor function is preserved below the neurologic level, however, more than half of key muscles below the neurologic level have a muscle grade less than 3 (i.e., not strong enough to move against gravity) |
| D | Incomplete: motor function is preserved below the neurologic level, and at least half of key muscles below the neurologic level have a muscle grade of 3 or more (i.e., joints can be moved against gravity) |
| E | Normal: motor and sensory functions are normal |

Thus, a patient presenting with a classification rating of A or B on the ASIA Impairment Scale has no motor function below the level of the injury.

In other embodiments, a patient suspected of having a CNS injury may have a score of ≤12 (e.g. 3 to 12) on the Glasgow Coma Scale (GCS). In still other embodiments, the patient may have a GCS score of ≤8 (e.g. 3 to 8). The GCS is a neurological scale commonly used to assess the level of consciousness of patients after injury or trauma. The scale is composed of three tests (eye, verbal and motor responses), each of which is assigned a value on a scale up to 6. The three values separately as well as their sum are considered. The lowest possible GCS score (the sum) is 3 (deep coma or death), while the highest is 15 (fully awake person). A GCS score<9 is indicative of severe brain injury whereas a GCS score≥13 is indicative of minor brain injury. A GCS score between 9-12 is generally indicative of a moderate brain injury.

A patient suspected of having a CNS injury may have one or more signs and symptoms of CNS injury, such as temporary loss of consciousness, confusion, disorientation, memory or concentration problems, headache, dizziness, loss of balance, nausea or vomiting, sensory disruptions (e.g. blurred vision, ringing in the ears, bad taste in the mouth, loss of sensation in limbs), loss of motor function, sensitivity to light or sound, mood changes or mood swings, depression or anxiety, fatigue, drowsiness, and sleep disturbances.

In some embodiments, the level, concentration, or abundance of one or more inflammasome proteins is measured in a biological sample obtained from a patient (e.g. a patient suspected of having or suffering from a CNS injury). In particular embodiments, the levels, concentrations, or abundance of one or more inflammasome proteins is indicative of the severity of CNS injury in the patient. A CNS injury includes, but is not limited to, a traumatic brain injury, a stroke-related injury, a cerebral aneurism-related injury, a spinal cord injury (e.g. contusions, compressions, lacerations), concussion-related injury (including post-concussion syndrome), cerebral ischemia, injury resulting from neurodegenerative diseases (including Parkinson's disease, Dementia Pugilistica, Huntington's disease, Alzheimer's disease, Creutzfeldt-Jakob disease), seizure-related injuries, multiple sclerosis, amyotrophic lateral sclerosis, and other CNS traumas. In certain embodiments, the levels, concentrations, or abundance of one or more inflammasome proteins is indicative of the severity of traumatic brain injury or spinal cord injury in the patient.

As used herein, "biological sample" refers to any bodily fluid or tissue obtained from a patient or subject. A biological sample can include, but is not limited to, whole blood, red blood cells, plasma, serum, peripheral blood mononuclear cells (PBMCs), urine, saliva, tears, buccal swabs, CSF, CNS microdialysate, and nerve tissue. In one embodiment, the biological sample is CSF, saliva, serum, plasma, or urine. In certain embodiments, the biological sample is CSF.

In some embodiments, the measured level, concentration, or abundance of one or more inflammasome proteins in the biological sample is used to prepare an inflammasome protein profile, wherein the profile is indicative of the severity of a CNS injury in the patient or the patient's prognosis or recovery potential from a CNS injury. The inflammasome protein profile may comprise the level, abundance, or concentration of one or more inflammasome proteins measured in the patient's sample optionally in relation to a pre-determined value or range of reference values as described herein. In certain embodiments, the inflammasome proteins in the profile include NLRP1 (NALP-1), ASC, and/or caspase-1 (e.g. p20 subunit of caspase-1). In one particular embodiment, the inflammasome protein profile comprises the level, abundance, or concentration of each of NLRP1 (NALP-1), ASC, and caspase-1 (e.g. p20 subunit of caspase-1).

In one aspect of the invention, the method of evaluating a patient suspected of having a CNS injury comprises determining the presence or absence of a protein signature associated with a CNS injury or a more severe CNS injury based on the measured level, abundance, or concentration of one or more inflammasome proteins in the patient sample or on the inflammasome protein profile prepared from the patient's sample. In certain embodiments, the protein signature comprises an elevated level of at least one inflammasome protein. The level of said at least one inflammasome protein in the protein signature may be enhanced relative to the level of the protein in a control sample or relative to a pre-determined reference value or range of reference values as further described herein. The protein signature may, in certain embodiments, comprise an elevated level for each of caspase-1 (e.g. p20 subunit of caspase-1), NLRP1, and ASC. Patients who exhibit the protein signature may be selected or identified as having a CNS injury or a more severe CNS injury.

The level or concentration of at least one inflammasome protein can be assessed at a single time point (e.g. after a potential CNS injury) and compared to a pre-determined reference value or range of reference values or can be assessed at multiple time points (e.g. two, three, four, five or more) after a potential CNS injury and compared to a pre-determined reference value or to previously assessed values. For instance, a biological sample for measuring levels or concentrations of inflammasome proteins can be obtained from a patient within one hour of a potential CNS injury to two weeks following a potential CNS injury. In some embodiments, the biological sample is obtained within one day, two days, three days, four days, five days, six days, seven days, ten days, or twelve days of a CNS injury or potential injury.

As used herein, "pre-determined reference value" refers to a pre-determined value of the level or concentration of an inflammasome protein ascertained from a known sample. For instance, the pre-determined reference value can reflect the level or concentration of an inflammasome protein in a sample obtained from a control subject (i.e., an uninjured, healthy subject). The control subject may, in some embodiments, be age-matched to the patients being evaluated. Thus, in particular embodiments, the measured level or concentration of at least one inflammasome protein is compared or determined relative to the level or concentration of said at least one inflammasome protein in a control sample (i.e. obtained from an uninjured subject).

In other embodiments, the pre-determined reference value or range of reference values can reflect the level or concentration of an inflammasome protein in a sample obtained from a patient with a known severity of CNS injury as assessed by clinical measures or post mortem analysis. A pre-determined reference value can also be a known amount or concentration of an inflammasome protein. Such a known amount or concentration of an inflammasome protein may correlate with an average level or concentration of the inflammasome protein from a population of control subjects or a population of patients with known levels of injury. In another embodiment, the pre-determined reference value can be a range of values, which, for instance, can represent a mean plus or minus a standard deviation or confidence interval. A range of reference values can also refer to individual reference values for a particular inflammasome protein across various levels of CNS injury severity. In certain embodiments, an increase in the level of one or more inflammasome proteins (e.g., NLRP1 (NALP-1), ASC, or caspase-1) relative to a pre-determined reference value or range of reference values is indicative of a more severe central nervous system injury.

In some embodiments, the method of assessing the severity of a CNS injury further comprises measuring the level or concentration of one or more proteins described in U.S. Patent Publication No. 2011/0177974, which is hereby incorporated by reference in its entirety, in addition to measuring the level or concentration of one or more inflammasome proteins. For instance, in certain embodiments, the method further comprises measuring the level or concentration of one or more proteins selected from ubiquitin C-terminal hydrolase Li; vesicular membrane protein p-24; synuclein; microtubule-associated protein; synaptophysin; Vimentin; Synaptotagmin; Synaptojanin-2; Synapsin2; CRMP1, 2; Amphiphysin-1; PSD95; PSD-93; Calmodulin dependent protein kinase II (CAMPK)-alpha, beta, gamma; Myelin basic protein (MBP); Myelin proteolipid protein (PLP); Myelin Oligodendrocyte specific protein (MOSP); Myelin Oligodendrocyte glycoprotein (MOG); myelin associated protein (MAG); NF-H; NF-L; NF-M; BIII-tubulin-1 or combinations thereof in the biological sample obtained from the patient in addition to measuring the level or concentration of one or more inflammasome proteins. Thus, the protein signature may comprise an elevated level of one or more of these proteins in addition to the elevated level of one or more inflammasome proteins. In other embodiments, the method further comprises measuring the level or concentration of one or more proteins selected from S-100β, neuron-specific enolase, neurofilament light chain, glial fibrillary acidic protein (GFAP) or combinations thereof in the biological sample obtained from the patient in addition to measuring the level or concentration of one or more inflammasome proteins. In one embodiment, the protein signature associated with a CNS injury or a more severe CNS injury comprises an elevated level of one or more proteins selected from S-100β, neuron-specific enolase, neurofilament light chain, glial fibrillary acidic protein (GFAP) in addition to an elevated level of one or more inflammasome proteins (e.g. NLRP1 (NALP-1), ASC, or caspase-1).

In other embodiments of the invention, the methods of assessing the severity of a CNS injury in a patient or evaluating a patient suspected of having a CNS injury further comprise administering a neuroprotective treatment to the patient based on the measured level of said at least one inflammasome protein or when a protein signature associated with a CNS injury or a more severe CNS injury is identified. Such neuroprotective treatments include drugs that reduce excitotoxicity, oxidative stress, and inflammation. Thus, suitable neuroprotective treatments include, but are not limited to, methylprednisolone, 17α-estradiol, 17β-estradiol, ginsenoside, progesterone, simvastatin, deprenyl, minocycline, resveratrol, and other glutamate receptor antagonists (e.g. NMDA receptor antagonists) and antioxidants. In some embodiments, neuroprotective treatments are neutralizing antibodies against an inflammasome protein or binding fragments thereof, such as those described in U.S. Patent Publication No. 2009/0104200, which is hereby incorporated by reference in its entirety. For instance, in one embodiment, the neuroprotective treatment is an anti-ASC antibody or fragment thereof. Anti-ASC antibodies include antibodies that specifically bind to amino acid residues 178-193 of rat ASC (accession number BAC43754), e.g., amino acid sequence ALRQTQPYLVTDLEQS (SEQ ID NO: 1), or antibodies that specifically bind to the amino acid sequence RESQSYLVEDLERS (SEQ ID NO:2) of human ASC. In another embodiment, the neuroprotective treatment is an anti-NLRP1 antibody or fragment thereof. Suitable neutralizing anti-NLRP1 antibodies or fragments thereof include antibodies that specifically bind to the amino acid sequence CEYYTEIREREREKSEKGR (SEQ ID NO:3) of human NLRP1 or the amino acid sequence MEESQSKEE-SNTEG (SEQ ID NO: 4) of rat NLRP1. The neutralizing antibodies or antibody fragments may be polyclonal antibodies, monoclonal antibodies, chimeric antibodies, humanized antibodies, single-chain variable fragments (scFvs) and the like. Aptamers that specifically bind to an inflammasome protein or epitope thereof (e.g., SEQ ID NOs: 1-4) may also be suitable neuroprotective treatments. Neuroprotective treatments also encompass therapeutic regimens or rehabilitative procedures, such as hypothermia treatment.

The success of, or response to, treatment can also be monitored by measuring the levels of at least one inflammasome protein. Accordingly, in some embodiments, the methods of evaluating a patient further comprise measuring the level of at least one inflammasome protein in a biological sample obtained from the patient following neuroprotective treatment, preparing a treatment protein signature associated with a positive response to the neuroprotective treatment, wherein the treatment protein signature comprises a reduced level of at least one inflammasome protein, and identifying patients exhibiting the presence of the treatment protein signature as responding positively to the neuroprotective treatment. A reduction in the level, abundance, or concentration of one or more inflammasome proteins (e.g. NLRP1, ASC, and caspase-1) is indicative of the efficacy of the neuroprotective treatment in the patient. The one or more inflammasome proteins measured in the sample obtained following treatment may be the same as or different than the inflammasome proteins measured in the sample obtained prior to treatment. The inflammasome protein levels may also be used to adjust dosage or frequency of a neuroprotective treatment.

The present invention also provides a method of determining a prognosis for a patient with a central nervous system injury. In one embodiment, the method comprises providing a biological sample obtained from the patient within a week of injury, and measuring the level of at least one inflammasome protein in the biological sample to prepare an inflammasome protein profile as described above, wherein the inflammasome protein profile is indicative of the prognosis of the patient. In certain preferred embodiments, the biological sample is obtained from the patient within one week, within five days, or within three days of injury. In some embodiments, an increase in the level of one or more inflammasome proteins (e.g., NLRP1, ASC, caspase-1, or combinations thereof) relative to a pre-determined reference value or range of reference values is indicative of a poorer prognosis. For instance, an increase of about 20% to about 300% in the level of one or more inflammasome proteins relative to a pre-determined reference value or range of reference values is indicative of a poorer prognosis. In one embodiment, increased levels of caspase-1, particularly the p20 subunit of active caspase-1, relative to a pre-determined reference value or range of reference values acutely after injury (i.e. within a week of injury) is indicative of a poorer prognosis.

In particular embodiments, an elevated level of at least one inflammasome protein relative to a pre-determined reference value or range of reference values is predictive of the patient's recovery potential or long-term outcome as assessed by the Glasgow Outcome Scale (GOS). The GOS is a scale that allows for the objective assessment of a patient's recovery following brain injury. The scale is comprised of scores ranging from 1 to 5 with the following descriptions:

| Score/Category | Description |
|---|---|
| 1-Death | Severe injury or death without recovery of consciousness |
| 2-Persistent Vegetative State | Severe damage with prolonged state of unresponsiveness and a lack of higher mental functions |
| 3-Severe Disability | Severe injury with permanent need for help with daily living |
| 4-Moderate Disability | No need for assistance in everyday life, employment is possible but may require special equipment |
| 5-Low Disability | Light damage with minor neurological and psychological deficits. |

In one embodiment, an elevated level of at least one inflammasome protein relative to a pre-determined reference value or range of reference values is predictive of the patient having a GOS score of 1 to 3 upon follow-up assessment (i.e. the patient having an unfavorable outcome, such as death or severe disability). In another embodiment, a reduced level of at least one inflammasome protein relative to a pre-determined reference value or range of reference values is predictive of the patient having a GOS score of 4 or 5 upon follow-up assessment (i.e. the patient having a favorable outcome, such as moderate to low disability). The inventors have found that the CSF levels of one or more inflammasome proteins within three days following a CNS injury are useful for predicting the long-term outcome or recovery potential of the patient. Elevated inflammasome proteins levels correlate with unfavorable outcomes for the patient, whereas reduced or low inflammasome protein levels correlate with favorable outcomes for the patient (Example 3).

The inflammasome proteins of the invention and other marker proteins can be measured in a biological sample by various methods known to those skilled in the art. For instance, proteins can be measured by methods including, but not limited to, liquid chromatography, gas chromatography, mass spectrometry, radioimmunoassays, immuno-fluorescent assays, FRET-based assays, immunoblot, ELISAs, or liquid chromatography followed by mass spectrometry (e.g., MALDI MS). One of skill in the art can ascertain other suitable methods for measuring and quantitating any particular biomarker protein of the invention.

The present invention also includes kits for preparing an inflammasome protein profile associated with CNS injury, such as spinal cord injury or traumatic brain injury. The kits may include a reagent for measuring at least one inflammasome protein and instructions for measuring said at least one inflammasome protein for assessing the severity of a central nervous system injury in a patient. As used herein, a "reagent" refers to the components necessary for detecting or quantitating one or more proteins by any one of the methods described herein. For instance, in some embodiments, kits for measuring one or more inflammasome proteins can include reagents for performing liquid or gas chromatography, mass spectrometry, immunoassays, immunoblots, or electrophoresis to detect one or more inflammasome proteins as described herein. In some embodiments, the kit includes reagents for measuring one or more inflammasome proteins selected from NLRP1, ASC, caspase-1, or combinations thereof.

In one embodiment, the kit comprises a labeled-binding partner that specifically binds to one or more inflammasome proteins, wherein said one or more inflammasome proteins are selected from the group consisting of NLRP1, ASC, caspase-1, and combinations thereof. Suitable binding partners for specifically binding to inflammasome proteins include, but are not limited to, antibodies and fragments thereof, aptamers, peptides, and the like. In certain embodiments, the binding partners for detecting NLPR1 are antibodies or fragments thereof, aptamers, or peptides that specifically bind to the amino acid sequence of SEQ ID NO: 3 or SEQ ID NO: 4 of human NLRP1 and rat NLRP1, respectively. In other embodiments, the binding partners for detecting ASC are antibodies or fragments thereof, aptamers, or peptides that specifically bind to the amino acid sequence of SEQ ID NO: 1 or SEQ ID NO: 2 of rat ASC and human ASC, respectively. Labels that can be conjugated to the binding partner include metal nanoparticles (e.g., gold, silver, copper, platinum, cadmium, and composite nanoparticles), fluorescent labels (e.g., fluorescein, Texas-Red, green fluorescent protein, yellow fluorescent protein, cyan fluorescent protein, Alexa dye molecules, etc.), and enzyme labels (e.g., alkaline phosphatase, horseradish peroxidase, beta-galactosidase, beta-lactamase, galactose oxidase, lactoperoxidase, luciferase, myeloperoxidase, and amylase).

In some embodiments, the kit can include reagents for measuring one or more inflammasome proteins in CSF samples. In other embodiments, the kits can include reagents for measuring one or more inflammasome proteins in other patient samples including nerve tissue, CNS microdialysate, blood, saliva, serum, plasma, or urine. In still other embodiments, the kits further comprise a set of reference values to which the measured level of one or more inflammasome proteins can be compared.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1. Inflammasome Proteins are Secreted into Cerebrospinal Fluid after Spinal Cord Injury To determine whether NLRP1 inflammasome proteins were present in cerebrospinal fluid (CSF) following spinal cord injury (SCI), CSF samples from seven patients with SCI or control patients were analyzed for levels of nucleotide-binding leucine-rich repeat pyrin domain containing protein 1 (NLRP1; also known as NAcht leucine-rich-repeat protein 1 (NALP-1)), apoptosis-associated speck-like protein containing a caspase recruitment domain (ASC), and caspase-1. The American Spinal Cord Injury Association (ASIA) scale of the SCI patients at admission to the emergency department ranged from AIS A to B. Information regarding the diagnosis, procedures and outcomes of the patients is shown in Table 1. None of the patients had any complications. CSF from uninjured individuals was obtained as a control from three males and two females ranging from 67 to 91 years old.

For detection of inflammasome proteins, CSF samples were prepared with Laemali buffer. Immunoblot analysis was carried with the Criterion system (Bio-Rad) as described previously (de Rivero Vaccari et al., 2008) using antibodies (1:1000 dilution) to NLRP1 (Bethyl Laboratories), Caspase-1 (Imgenex) and ASC (Santa Cruz). Proteins were resolved in 14-20% TGX Criterion precasted gels (Bio-Rad), transferred to polyvinylidene difluoride (PVDF) transfer membranes (Tropifluor—Applied Biosystems) and placed in blocking buffer (PBS, 0.10% Tween-20, 0.4% I-Block (Applied Biosystems) and then incubated for one hour with primary antibodies. Membranes were then incubated for one hour with anti-mouse, anti-rat or anti-rabbit horseradish peroxidase (HRP)-linked antibodies. Signal visualization was performed by enhanced chemiluminescence.

Immunoblot analysis of control CSF samples (n=5) revealed very low levels of NLRP1 inflammasome proteins (FIG. 1). In contrast, immunoblot analysis of samples from 6 different SCI patients showed an increase in the levels of NLRP1, caspase-1 and ASC in the CSF when compared to CSF from control subjects. It should be noted that patients 2, 3 and 4 (FIG. 1) did not show increased levels of caspase-1 acutely (day 0 through day 2) after SCI. Interestingly, these patients demonstrated stark motor improvement at 2 days after SCI. Patients 1, 5, and 6 showed increased levels of caspase-1, ASC and NLRP1 inflammasome proteins acutely after SCI and these individuals had a poor prognosis and did not show motor improvements. Thus, it appears that individuals that present with low levels of caspase-1 in CSF acutely after SCI may have a better prognosis than those individuals who show increased levels of this biomarker.

The results from these experiments show that protein levels of NLRP1, ASC, and caspase-1 in CSF are increased following injury to the central nervous system and suggest that levels of these inflammasome proteins can serve as biomarkers of the severity of neuronal damage following injury thereby directing treatment and rehabilitation efforts, monitoring response to treatment, and aiding in the determination of prognosis of recovery in injured patients.

Example 2. Immunohistochemical Expression of NLRP1 Inflammasome Proteins in Spinal Cords After Injury Spinal cord sections were obtained from nine decedents (8 males and 1 female with ages ranging from 20 to 77 years) who had injury to the spinal cord due to vertebral fractures. The spinal cord injury was assessed microscopically, using bright field optics, by examining one H&E or H&E/DAB-stained section from the lesion center of each case or from cervical, thoracic and lumbar sections from control cases. The spinal cord injuries were classified on the basis of their histological appearance as "contusion/cyst," massive compression, or laceration (Fleming et al., 2006). Contusional injuries were characterized by an intact pia and relative preservation of the anatomical relations of various elements of the spinal cord, and variable degrees of injury ranging from involvement of the entire cross-sectional area to large usually asymmetric areas of tissue damage. Massive compression injuries were characterized by disruption of the pia and severe distortion and disruption of spinal cord parenchyma. Laceration injuries, which by definition were perforating or penetrating injuries caused by weapons or projectiles, were associated with breaching of the pia and linear tearing of the cord tissue.

All tissue samples had been removed within 24 h of death and fixed in neutral buffered formalin. Blocks from the spinal cords were dehydrated, embedded in paraffin wax, cut into 6 μm thick sections and placed on positively charged glass slides. One set of sections was stained with hematoxylin-eosin (H&E) and the remaining sets were used for immunohistochemistry. Paraffin-embedded sections were stained with anti-NLRP1 (Bethyl Laboratories as described in de Rivero Vaccari et al. 2008), anti-caspase-1 (Upstate), and anti-ASC (Chemicon) using diaminobenzidine (DAB) as the chromophore and hematoxylin. Negative controls included sections in which the primary antibody was omitted and sections incubated with isotype-matched antibodies (1:100-1:10,000 IgG). These positive and negative controls were processed with every batch of immunohistochemical slides.

In all cases, tissue samples from the center of injury and at various distances above and below the injury were obtained. The data from tissue from the center of the lesion were used to compare the inflammatory responses between cases whereas those from the remote, uninjured segments of the spinal cord served as within-case controls. Between-case comparison of the remote samples was not possible because, for different cases, the distance of these samples from the lesion center was variable.

Figure 2:
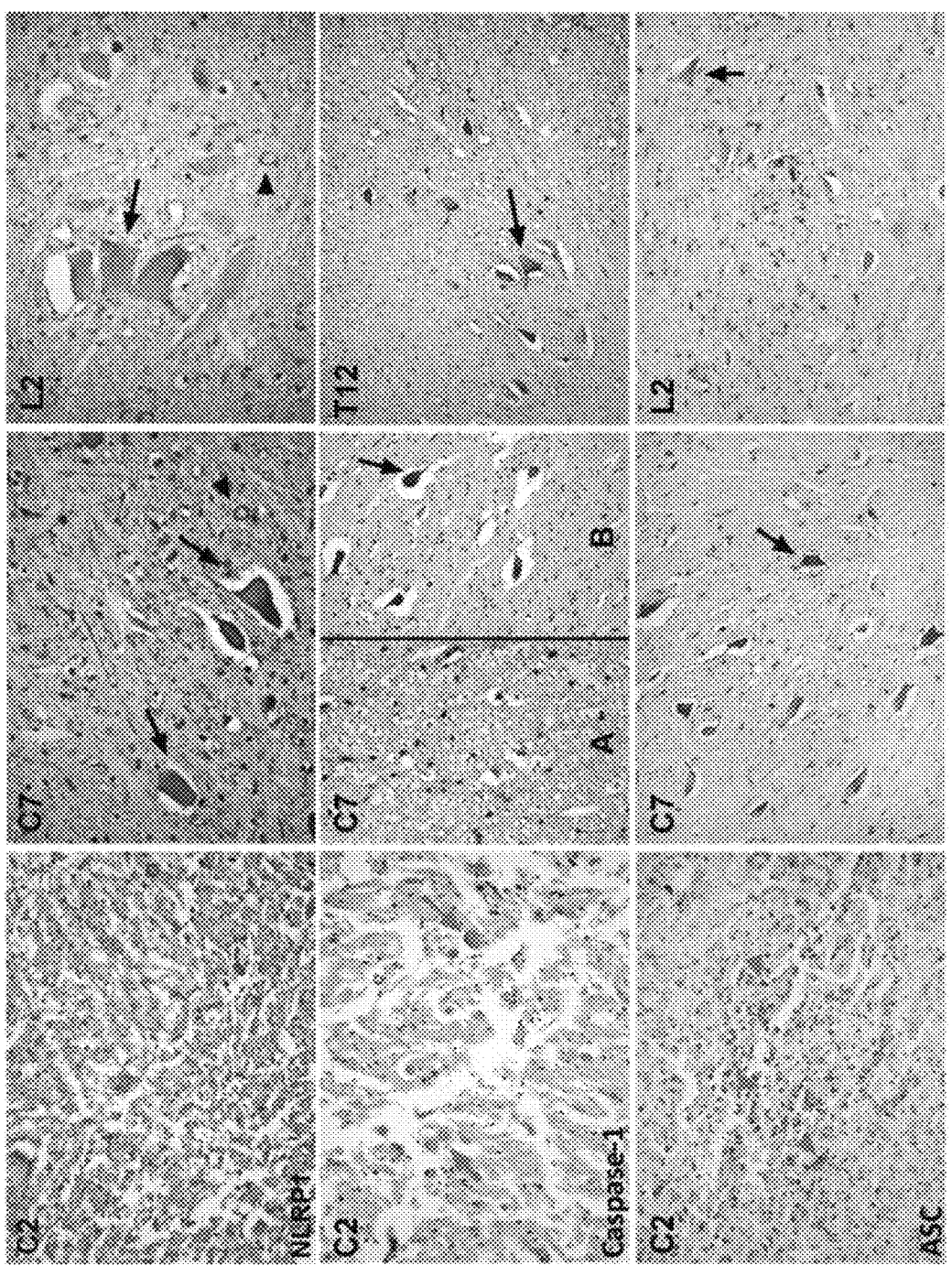
FIG. 2. NLRP1 inflammasome proteins are expressed in cells of the CNS. Spinal cord sections were obtained from decedents that had injury to the spinal cord. Immunohistochemical analysis combined with light microscopy indicates that NLRP1 is expressed in neurons of the ventral horn (black arrows) myelinated axons (black arrow heads) and oligodendrocytes (yellow arrows) (top panel). Caspase-1 is expressed in swollen axons (spheroids, blue arrows), motor neurons (black arrows) and in oligodendrocytes (yellow arrows) (central panel). ASC is present in neurons in the ventral horn (black arrows), white matter oligodendrocytes (yellow arrow) and macrophages/microglia (blue arrow heads) (bottom panel).

Immunohistochemical analysis combined with light microscopy indicated that NLRP1 is expressed in neurons of the ventral horn (black arrows), myelinated axons (arrow heads) and oligodendrocytes (yellow arrows) in injured spinal cords (FIG. 2). Moreover, NLRP1 immunoreactivity in areas of the penumbra (C7) was higher than in areas distant to the epicenter (L2).

DAB immunoreactivity for caspase-1 was detected in swollen axons (spheroids, blue arrows) (FIG. 2), and arterioles (not shown). At areas of the penumbra, caspase-1 staining is present in motor neurons (black arrows) of the ventral horn, and in the white matter in oligodendrocytes (yellow arrows). Caspase-1 immunoreactivity in oligodendrocytes (yellow arrows) was the same at all levels of the spinal cords examined, regardless of proximity to the epicenter. At areas distant to the epicenter (T12), caspase-1 was also present in motor neurons (black arrows) but with decreased immunoreactivity than the penumbra (C7). This finding indicates that caspase-1 immunoreactivity in neurons decreases as the distance to the epicenter increases, similarly to NLRP1.

At areas of the penumbra (C7) and distant to the epicenter (L2), neurons in the ventral horn (black arrows) and white matter oligodendrocytes (yellow arrow) showed ASC immunoreactivity. In addition, ASC was also present in macrophages/microglia at the epicenter (blue arrow heads). Moreover, ASC immunoreactivity was also detected in the substantia gelatinosa (dorsal horn) at C7 and L2 (not shown).

Neuroinflammation has been considered to play a critical role in the pathogenesis of SCI and TBI, but the role of the innate immune response has not been examined directly. The innate immune system senses microbial and viral pathogen-associated molecular patterns and danger signals released from damaged or stressed cells to trigger conserved intracellular signaling pathways that drive proinflammatory responses that are critical for productive innate and adaptive immunity. Excessive inflammatory responses become deleterious leading to tissue destruction. The results of this experiment provide evidence demonstrating that the NLRP1 inflammasome signaling system is activated in the innate immune response in damaged human spinal cord and brain tissue after trauma. These findings support the idea that activation of the NLRP1 inflammasome signaling system is an early event in spinal cord and brain pathology and that these proteins may serve as biomarkers for SCI and TBI in humans.

Example 3. Inflammasome Proteins in Cerebrospinal Fluid of Brain-Injured Patients are Biomarkers of Functional Outcome To determine whether inflammasome proteins may serve as biomarkers for other types of central nervous system injury, a total of 45 CSF samples were collected from 23 traumatic brain injury (TBI) patients on the day of injury and up to three days after the injury and analyzed by immunoblot for levels of NALP-1 (also known as NLRP1), ASC, and caspase-1. Each of the patients presented with the following inclusion criteria: severe or moderate head trauma (Glasgow Coma Scale (GCS) score≤12), age 1 month to 65 years, and ventriculostomy. Twenty-two of the patients suffered severe brain trauma (GCS score≤8) and 1 suffered moderate brain trauma (moderate TBI GCS score range 9-12). Nine patients (5 men and 4 women) with a mean age of 66.3 years (range 29-91 years) served as controls. Control patients required a ventriculostomy for nontraumatic pathology. Patients with acute meningitis, cerebral vasculitis, or other recent CNS infection were excluded. Information regarding patient demographics, intracranial pathology, GCS score at presentation, and Glasgow Outcome Scale (GOS) score at 5 months post-injury is shown in Table 2.

Figure 3:
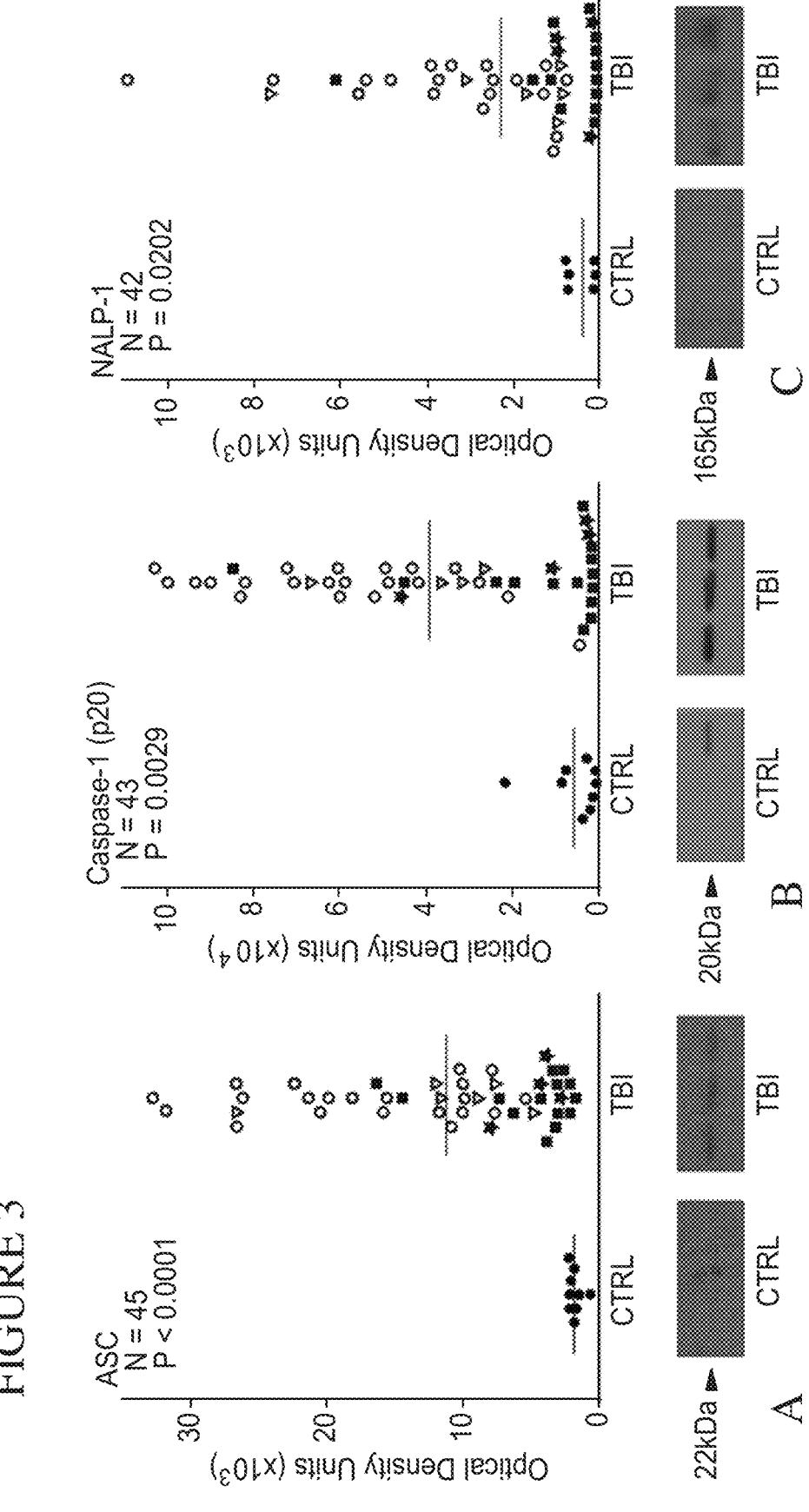
FIG. 3. Scatter plots of expression of inflammasome proteins in controls and patients with TBI. Samples were immunoblotted for ASC (A), caspase-1 (B), and NALP-1 (C). The p values in the upper left corner represent results of a Mann-Whitney U-test. Densitometric analysis revealed a significant increase in expression of ASC, caspase-1 (p20), and NALP-1 in the CSF of patients with TBI compared with nontrauma controls. Solid lines denote mean values for each group. Different shapes correspond to patient outcomes at 5 months postinjury. Representative immunoblots are shown. Samples were run on the same gel but were noncontiguous. N=the number of TBI samples analyzed; ★=GOS Score 5; ■=GOS Score 4; ●=GOS Score 3; ▽=GOS Score 1.

Cerebrospinal fluid samples were collected within 12 hours of injury and up to 72 hours after injury. Samples were centrifuged at 2000 g for 10 minutes at 4° C. to pellet cellular bodies and debris. Supernatants were resolved by gel electrophoresis and immunoblotted as previously described (de Rivero Vaccari et al., 2008). Quantification of band density was performed with UNSCAN-IT gel digitizing software (Silk Scientific). Due to the low volume of sample available, NALP-1 was analyzed in 6 of the 9 controls, caspase-1 was analyzed in 43 of the 45 TBI samples, and NALP-1 was analyzed in 42 of the 45 TBI samples. Immunoblot analysis shows that the inflammasome proteins ASC, caspase-1 (p20), and NALP-1 are present in the CSF of patients with TBI and nontrauma controls. Quantitative data from a densitometric analysis are shown in FIG. 3. Expression of the 22-kD isoform of ASC (FIG. 3A), the p20 subunit of cleaved caspase-1 (FIG. 3B), and NALP-1 (FIG. 3C) is significantly elevated in the CSF of TBI patients compared with nontrauma controls ($p < 0.0001$, $p = 0.0029$, and $p = 0.0202$, respectively).

Figure 4:
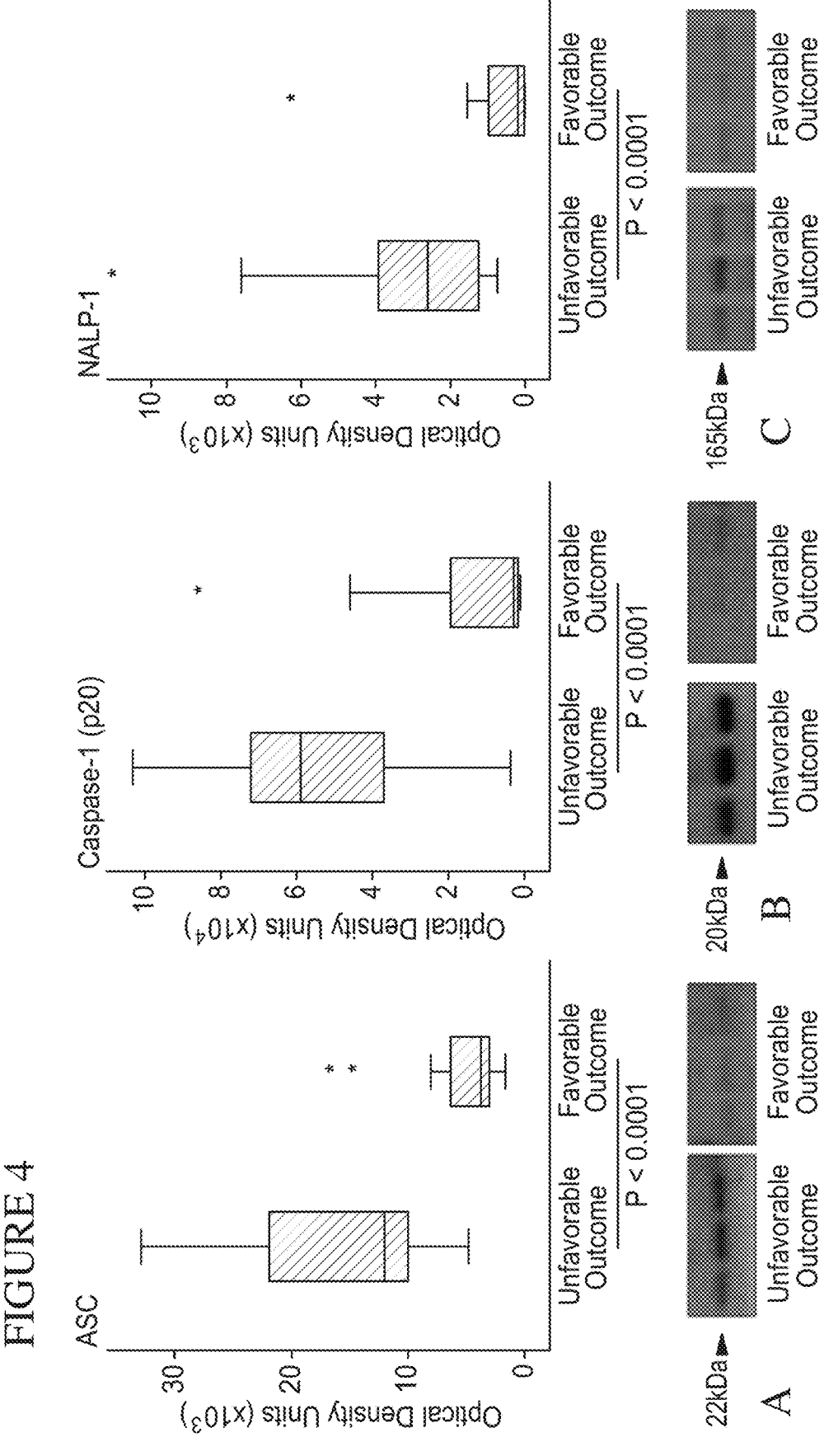
FIG. 4. Box plots of expression of inflammasome proteins sorted by outcome category. The ends of the whiskers represent the lowest datum within 1.5 interquartile range of the lower quartile and the highest datum within 1.5 interquartile range of the upper quartile. The asterisks represent the outliers. Mann-Whitney U-tests indicate higher expression of ASC (A), caspase-1 (p20) (B), and NALP-1 (C) are significantly associated with an unfavorable outcome 5 months after injury (p<0.0001). Representative immunoblots for each protein are shown. Samples were run on the same gel but were noncontiguous.

To determine if the levels of inflammasome components correlate with outcome, we grouped study participants by outcome category (GOS Scores 1 and 3, unfavorable outcome; GOS Scores 4 and 5, favorable outcome). At 5 months postinjury, 3 patients had a GOS score of 1 (death), 11 patients had a GOS score of 3 (severe disability), 6 patients had a GOS score of 4 (moderate disability), and 3 patients had a GOS score of 5 (good recovery). Within the sample of patients with TBI, no patient remained with a GOS score of 2 (persistent vegetative state). We detected significantly higher levels of ASC (FIG. 4A), caspase-1 (p20) (FIG. 4B), and NALP-1 (FIG. 4C) in the CSF of TBI patients with unfavorable outcomes, including death and severe disability with complete dependence on others for activities of daily living ($p < 0.0001$).

Figure 5:
FIG. 5. Scatter plots and estimated linear regression of ASC (A), caspase-1 (p20) (B), and NALP-1 (C) expression in the CSF with GOS score. Probability values of the linear regression are shown in the top left of each graph. Expression of each protein correlated significantly with GOS score at 5 months post-injury. The p values on the x axis represent post hoc comparisons of a Kruskal-Wallis test. Representative immunoblots are shown. Samples were run on the same gel but were noncontiguous.

To further understand the relationship between outcome and inflammasome proteins, we constructed modified scatter plots of expression levels of ASC, caspase-1 (p20), and NALP-1 and GOS (FIG. 5). A calculated linear regression line is shown for each plot. Linear regression analysis shows that expression of ASC (FIG. 5A; $p < 0.05$), caspase-1 (p20) (FIG. 5B; $p < 0.01$), and NALP-1 (FIG. 5C; $p < 0.05$) correlate significantly with outcome at 5 months. Post hoc, the Dunn multiple comparison tests following a Kruskal-Wallis test showed that the levels of ASC are significantly higher in patients with severe disability (GOS Score 3) compared with patients with moderate disability (GOS Score 4) ($p < 0.001$) and patients with mild to no disability (GOS Score 5) ($p < 0.05$). Similarly, expression levels of caspase-1 (p20) and NALP-1 are significantly higher in patients with severe disability (GOS Score 3) than in those with moderate disability (GOS Score 4) ($p < 0.001$).

The results of this study show that inflammasome proteins (e.g. ASC, NALP-1, and caspase-1) are acutely elevated (e.g. within 72 hours) in the CSF of patients with TBI as compared with nontrauma controls. Elevation of these proteins likely reflects the extent of neuroinflammation, suggesting that inflammasome proteins can serve as acute biomarkers of CNS injury. These findings are clinically relevant, as CSF biomarkers are more specific indicators of neuropathology than serum biomarkers. Cerebrospinal fluid directly bathes the brain, closely reflecting the extracellular milieu and biochemical changes that are specific to the CNS. Sampling the CSF eliminates influences of multiorgan trauma or other systemic pathology represented in the serum, which is significant as patients with TBI often present with trauma to other organ systems.

The results also demonstrate that levels of inflammasome proteins are significantly higher in the CSF of patients who have died and those with severe disability than in patients with moderate to no disability, suggesting that inflammasome activation produces chronic neuroinflammation, contributing to secondary injury and poor outcome 5 months after TBT. The extent of acute elevation of these proteins can predict an unfavorable versus favorable outcome. Such markers could also direct treatment and rehabilitation efforts. The clinician would target therapies to patients identified as having a greater risk of inflammation-mediated secondary injury.

Response to treatment could be monitored by following the levels of ASC, active caspase-1, and NALP-1 in the CSF. One such treatment, therapeutic hypothermia, attenuates the endogenous inflammatory response of the CNS to TBI by decreasing cytokine production and reducing activation of astrocytes and microglia (Aibiki et al., 1999; Goss et al., 1995; Kumar et al., 1997; Truettner et al., 2005), and cortical neurons exposed to moderate hypothermia in culture show a decrease in activation of the inflammasome (Tomura et al., in press). Thus, ASC, active caspase-1, and NALP-1 can serve as objective, biochemical indicators of treatment efficacy for patients with CNS injury.

Figure 6:
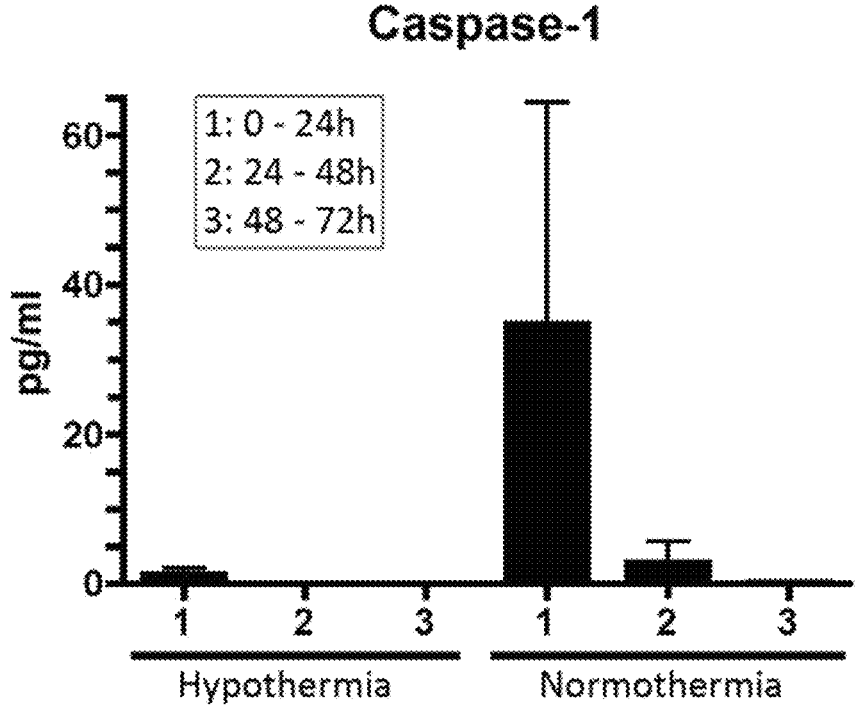
FIG. 6. Caspase-1 levels in CSF one, two, and three days following TBI in pediatric patients receiving hypothermia treatment or no treatment (normothermia).

Example 4. Hypothermia Decreases Caspase-1 Activation after Traumatic Brain Injury in Pediatric Patients To evaluate whether inflammasome proteins, such as caspase-1, can also be used to monitor treatment efficacy in TBI patients, CSF caspase-1 levels obtained from pediatric patients who received hypothermia treatment following TBI were compared to those obtained from pediatric patients who did not receive treatment following TBI. Cerebrospinal fluid of pediatric patients (ages 0.1 to 16 years) was obtained at different times after traumatic brain injury (day 1, 2 and 3). Patients were divided into those that received hypothermia treatment and those who did not (normothermia). As shown in FIG. 6, the data indicate that within 24 hours after injury the levels of caspase-1 were lower in the hypothermia group when compared to the normothermia group. Thus post-traumatic therapeutic hypothermia lowers the levels of caspase-1 activation after brain injury, consistent with findings that those patients that receive hypothermia treatment present better outcomes when compared to those patients who do not get the hypothermia treatment.

All publications, patents and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

TABLE 1

Spinal Cord Injury Subjects

| Patient | Age | Gender | Race | Mechanism of Injury | Spinal Injury | AIS Grade | Level | Surgery | Hypothermia | Other injuries | Exam at Rehab D/C |
|---------|-----|--------|------|---------------------|---------------|-----------|-------|---------|-------------|----------------|-------------------|
| 1 | 43 | M | Black | Auto vs. Pedestrian | C7/T1 bilateral jumped facets | A | C7 | C4-T2 Laminectomy w/instrumented fusion | Yes | None | C7 ASIA A |
| 2 | 38 | M | Hispanic | Fall from height | T3 & T4 Burst fractures | B | T3 | T1-6 Laminectomy w/instrumented fusion | No | None | T3 ASIA D |
| 3 | 21 | M | White | Driving accident | C5/6 Fracture dislocation | A | C5 | C5/6 Anterior disectomy & fusion | Yes | None | C5 ASIA C |
| 4 | 19 | M | Black | Motor vehicle accident | C4/5 Bilateral jumped facets | B | C4 | C4/5 Anterior disectomy & fusion | No | None | C4 ASIA D |
| 5 | 22 | M | White | Rugby accident | C5/6 Bilateral jumped facets | A | C5 | C5/6 Anterior disectomy & fusion | Yes | None | C6 ASIA A |
| 6 | 48 | M | Hispanic | Motorcycle vs. Pedestrian | T1/2 Fracture dislocation | A | T3 | C5-T2 Laminectomy w/instrumented fusion | No | Degloving injury and fractures of face | T3 ASIA B |

TABLE 2

Summary of demographic data in patients with TBI*

| Case No. | Age (yrs), Sex | Race | Mechanism of Injury | GCS Score† | GOS Score‡ | Intracranial Pathology |
|----------|----------------|------|---------------------|------------|------------|------------------------|
| 1 | 26, M | White | MVA | 3 | 4 | bilat temporal cortical contusions, SAH, SDH |
| 2 | 22, M | Hispanic | motorcycle accident | 3 | 4 | SDH, diffiffuse SAH |
| 3 | 19, F | Hispanic | MVA | 7 | 3 | fronto- & temporoparietal & basal ganglia hemorrhagic contusions, frontoparietal SAH |
| 4 | 30, F | Hispanic | MVA | 8 | 4 | scattered SAH, diffuse cerebral edema |
| 5 | 21, M | Hispanic | motorcycle accident | 5 | 3 | frontal SDH & SAH |
| 6 | 17, F | Hispanic | MVA | 4 | 3 | diffuse extraaxial & intraparenchymal hemorrhage |
| 7 | 26, M | Hispanic | MVA | 8 | 3 | diffuse SAH, IVH, & parenchymal hemorrhagic contusions |
| 8 | 36, M | White | ATV accident | 3 | 5 | SDH, SAH, & diffuse cerebral edema |
| 9 | 16, M | Hispanic | MVA | 7 | 5 | frontotemporal SDH, frontal lobe contusion, cerebral edema |
| 10 | 22, M | Hispanic | MVA | 3 | 3 | SDH |
| 11 | 36, M | Black | Gunshot wound | 3 | 1 | SDH, bullet fragments in frontal lobe |
| 12 | 54, M | Hispanic | Fall | 3 | 3 | frontal hemorrhagic contusions, parietooccipital hemorrhagic contusion, SDH, brain edema |
| 13 | 62, M | Black | MVA | 8 | 3 | diffuse frontoparietal hemorrhage, frontal & parietal lobe hemorrhagic contusions |
| 14 | 19, F | White | Assault | 8 | 3 | temporal & frontal lobe hemorrhagic contusions, frontotemporal SAH, frontal dural hematoma |
| 15 | 20, M | Hispanic | Motorcycle accident | 6 | 4 | bone fragments in frontoparietal brain parenchyma, scattered frontoparietal SAH, hemorrhagic contusions |
| 16 | 28, M | Hispanic | Motorcycle accident | 4 | 3 | SDH |
| 17 | 21, M | Black | MVA | 5 | 4 | mild cerebral edema |
| 18 | 45, M | Hispanic | Gunshot wound | 8 | 3 | bullet fragments in occipital lobe, occipital SDH, minimal parietal & occipital pneumocephalus |
| 19 | 21, M | White | MVA | 3 | 3 | diffuse axonal injury, scattered SAH, parietal SDH, mild hydrocephalus |
| 20 | 17, M | Hispanic | Sports injury | 4 | 4 | SDH, SAH, diffuse cerebral edema |
| 21 | 19, F | Hispanic | MVA | 11 | 5 | bone fragments in frontal lobe parenchyma, frontal lobe contusion, edema, pneumocephalus |

TABLE 2-continued

Summary of demographic data in patients with TBI*

| Case No. | Age (yrs), Sex | Race | Mechanism of Injury | GCS Score† | GOS Score‡ | Intracranial Pathology |
|---|---|---|---|---|---|---|
| 22 | 65, M | White | MVA | 7 | 1 | parietal SDH, SAH, parietal hemorrhagic contusion, uncal herniation |
| 23 | 18, M | White | MVA | 3 | 1 | diffuse axonal injury, scattered hemorrhagic contusions in frontal, temporal, parietal lobes & corpus callosum, IVH |

*IVH = intraventricular hemorrhage;
SAH = subarachnoid hemorrhage;
SDH = subdural hematoma.
MVA = motor vehicle accident;
ATV = all terrain vehicle
†Obtained on admission.
‡Assessed at 5 months postinjury.

REFERENCES

Abulafia D P, de Rivero Vaccari J P, Lozano J D, Lotocki G, Keane R W, Dietrich W D. Inhibition of the inflammasome complex reduces the inflammatory response after thromboembolic stroke in mice. J Cereb Blood Flow Metab 29:534-544, 2009.

Aibiki M, Maekawa S, Ogura S, Kinoshita Y, Kawai N, Yokono S: Effect of moderate hypothermia on systemic and internal jugular plasma IL-6 levels after traumatic brain injury in humans. J Neurotrauma 16:225-232, 1999.

Arend W P, Palmer G, Gabay C. IL-1, IL-18, and IL-33 families of cytokines. Immunol Rev 223:20-38, 2008.

Bianchi M E. DAMPs, PAMPs and alarmins: all we need to know about danger. J Leukoc Biol 81:1-5, 2007.

Brain Trauma Foundation, American Association of Neurological Surgeons, Joint Section on Neurotrauma and Critical Care: Initial management. J Neurotrauma 17:463-469, 2000.

Cao F, Yang X F, Liu W G, Hu W W, Li G, Zheng X J, Shen F, Zhao X Q, Lv S T. Elevation of neuron-specific enolase and S-100beta protein level in experimental acute spinal cord injury. J Clin Neurosci 15:541-544, 2008.

Cornefjord M, Nyberg F, Rosengren L, Brisby H. Cerebrospinal fluid biomarkers in experimental spinal nerve root injury. Spine (Phila Pa 1976) 29:1862-1868, 2004.

de Rivero Vaccari J P, Lotocki G, Alonso O F, Bramlett H M, Dietrich W D, Keane R W. Therapeutic neutralization of the NLRP1 inflammasome reduces the innate immune response and improves histopathology after traumatic brain injury. J Cereb Blood Flow Metab 29:1251-1261, 2009.

de Rivero Vaccari J P, Lotocki G, Marcillo A E, Dietrich W D, Keane R W. A molecular platform in neurons regulates inflammation after spinal cord injury. J Neurosci 28:3404-3414, 2008.

Goss J R, Styren S D, Miller P D, Kochanek P M, Palmer A M, Marion D W, et al: Hypothermia attenuates the normal increase in interleukin 1 beta RNA and nerve growth factor following traumatic brain injury in the rat. J Neurotrauma 12: 159-167, 1995.

Guez M, Hildingsson C, Rosengren L, Karlsson K, Toolanen G. Nervous tissue damage markers in cerebrospinal fluid after cervical spine injuries and whiplash trauma. J Neurotrauma 20:853-858, 2003.

Kufer T A, Sansonetti P J. NLR functions beyond pathogen recognition. Nat Immunol 12:121-128, 2011.

Kumar K, Wu X, Evans A T: GFAP-immunoreactivity following hypothermic forebrain ischemia. Metab Brain Dis 12:21-27, 1997.

Li H, Willingham S B, Ting J P, Re F. Cutting edge: inflammasome activation by alum and alum's adjuvant effect are mediated by NLRP3. J Immunol 181:17-21, 2008.

Loy D N, Sroufe A E, Pelt J L, Burke D A, Cao Q L, Talbott J F, Whittemore S R. Serum biomarkers for experimental acute spinal cord injury: rapid elevation of neuron-specific enolase and S-100beta. Neurosurgery 56:391-397; discussion 391-397, 2005.

Ma J, Novikov L N, Karlsson K, Kellerth J O, Wiberg M. Plexus avulsion and spinal cord injury increase the serum concentration of S-100 protein: an experimental study in rats. Scand J Plast Reconstr Surg Hand Surg 35:355-359, 2001.

Martinon F, Burns K, Tschopp J. The inflammasome: a molecular platform triggering activation of inflammatory caspases and processing of proIL-beta. Mol Cell 10:417-426, 2002.

Nagy G, Dzsinich C, Selmeci L, Sepa G, Dzsinich M, Kekesi V, Juhasz-Nagy A. Biochemical alterations in cerebrospinal fluid during thoracoabdominal aortic cross-clamping in dogs. Ann Vase Surg 16:436-441, 2002.

Pouw M H, Hosman A J, van Middendorp J J, Verbeek M M, Vos P E, van de Meent H. Biomarkers in spinal cord injury. Spinal Cord 47:519-525, 2009.

Qu Y, Franchi L, Nunez G, Dubyak G R. Nonclassical IL-1 beta secretion stimulated by P2X7 receptors is dependent on inflammasome activation and correlated with exosome release in murine macrophages. J Immunol 179:1913-1925, 2007.

Silverman W R, de Rivero Vaccari J P, Locovei S, Qiu F, Carlsson S K, Scemes E, Keane R W, Dahl G. The pannexin 1 channel activates the inflammasome in neurons and astrocytes. J Biol Chem 284:18143-18151, 2009.

Skouen J S, Brisby H, Otani K, Olmarker K, Rosengren L, Rydevik B. Protein markers in cerebrospinal fluid in experimental nerve root injury. A study of slow-onset chronic compression effects or the biochemical effects of nucleus pulposus on sacral nerve roots. Spine (Phila Pa 1976) 24:2195-2200, 1999.

Teasdale G, Jennett B. Assessment of coma and impaired consciousness. A practical scale. Lancet 2:81-84, 1974.

Tomura S, de Rivero Vaccari J P, Keane R W, Bramlett H M, Dietrich W D: Effects of therapeutic hypothermia on inflammasome signaling after traumatic brain injury. J Cereb Blood Flow Metab [in press], 2012.

Truettner J S, Suzuki T, Dietrich W D: The effect of therapeutic hypothermia on the expression of inflammatory response genes following moderate traumatic brain injury in the rat. Brain Res Mol Brain Res 138:124-134, 2005.

Wakefield D, Gray P, Chang J, Di Girolamo N, McCluskey P. The role of PAMPs and DAMPs in the pathogenesis of acute and recurrent anterior uveitis. Br J Ophthalmol 94:271-274, 2010.

The invention claimed is:

1. A method of evaluating and treating a patient suspected of having a spinal cord injury or traumatic brain injury comprising:

providing a biological sample from a patient presenting with clinical symptoms consistent with a spinal cord injury or traumatic brain injury, wherein the biological sample is cerebrospinal fluid (CSF);

measuring the level of at least one inflammasome protein in the biological sample by immunoblot or ELISA, wherein the at least one inflammasome protein is selected from the group consisting of nucleotide-binding leucine-rich repeat pyrin domain containing protein 1 (NLRP1), apoptosis-associated speck-like protein containing a caspase recruitment domain (ASC), and caspase-1, or a combination thereof;

determining the presence or absence of a protein signature associated with a spinal cord injury or traumatic brain injury, wherein the protein signature comprises an elevated level of said at least one of the inflammasome proteins relative to a pre-determined reference value or range of reference values in a non-trauma patient as a control; and selecting patients exhibiting the presence of the protein signature as having a spinal cord injury or traumatic brain injury; and administering a neuroprotective treatment to the patient when said protein signature is identified.

2. The method of claim 1, wherein the protein signature comprises an elevated level for each of caspase-1, NLRP1, and ASC.

3. The method of claim 2, wherein the protein signature comprises an elevated level for the p20 subunit of caspase-1.

4. The method of claim 1, wherein said biological sample is obtained within one week of the suspected injury.

5. The method of claim 1, wherein said biological sample is obtained within five days of the suspected injury.

6. The method of claim 1, wherein said biological sample is obtained within three days of the suspected injury.

7. The method of claim 1, wherein the patient has an A or B rating on the American Spinal Cord Injury Association (ASIA) Impairment Scale.

8. The method of claim 1, wherein the patient has a Glasgow Coma Scale (GCS) score of 3 to 12.

9. The method of claim 8, wherein the patient has a GCS score of 3 to 8.

10. The method of claim 1, wherein the patient is a pediatric patient.

11. The method of claim 1, wherein the neuroprotective treatment is hypothermia, methylprednisolone, 17α-estradiol, 17β-estradiol, ginsenoside, progesterone, simvastatin, deprenyl, minocycline, and resveratrol.

12. The method of claim 1, further comprising:

following neuroprotective treatment, measuring by immunoblot or ELISA the level of said at least one elevated inflammasome protein in the biological sample obtained from the patient wherein a decrease in the elevated level of said at least one inflammasome protein in the biological sample indicates the patient is responding positively to the neuroprotective treatment.

13. A method of determining a prognosis for a patient with a spinal cord injury or traumatic brain injury and treating said patient, said method comprising:

providing a cerebrospinal fluid (CSF) sample obtained from the patient within a week of injury; and measuring the level of at least one inflammasome protein in the CSF sample, wherein the inflammasome protein is selected from the group consisting of nucleotide-binding leucine-rich repeat pyrin domain containing protein 1 (NLRP1), apoptosis-associated speck-like protein containing a caspase recruitment domain (ASC), and caspase-1, or a combination thereof, wherein, when measured by immunoblot or ELISA relative to a pre-determined reference value or range of reference values in a non-trauma patient as a control, an elevated level of measured inflammasome protein is indicative of poor prognosis of the patient and a reduced level of measured inflammasome protein is indicative of better prognosis of the patient; and administering a neuroprotective treatment to the patient when said elevated protein signature is identified.

14. The method of claim 13, wherein an elevated level of at least one inflammasome protein relative to a pre-determined reference value or range of reference values is predictive of the patient having a Glasgow Outcome Scale (GOS) score of 1 to 3 upon follow-up assessment.

15. The method of claim 13, wherein said at least one inflammasome protein is the p20 subunit of caspase-1.

16. The method of claim 13, wherein a reduced level of at least one inflammasome protein relative to a pre-determined reference value or range of reference values is predictive of the patient having a GOS score of 4 or 5 upon follow-up assessment.

17. The method of claim 13, wherein the patient is a pediatric patient.

18. The method of claim 13, wherein the neuroprotective treatment is hypothermia, methylprednisolone, 17α-estradiol, 17β-estradiol, ginsenoside, progesterone, simvastatin, deprenyl, minocycline, and resveratrol.

* * * * *

SEQUENCE LISTING

```
Sequence total quantity: 4
SEQ ID NO: 1              moltype = AA  length = 16
FEATURE                   Location/Qualifiers
source                    1..16
                          mol_type = protein
                          organism = Rattus sp.
SEQUENCE: 1
ALRQTQPYLV TDLEQS                                          16

SEQ ID NO: 2              moltype = AA  length = 14
FEATURE                   Location/Qualifiers
source                    1..14
                          mol_type = protein
                          organism = Homo sapiens
SEQUENCE: 2
RESQSYLVED LERS                                            14

SEQ ID NO: 3              moltype = AA  length = 19
FEATURE                   Location/Qualifiers
source                    1..19
                          mol_type = protein
                          organism = Homo sapiens
SEQUENCE: 3
CEYYTEIRER EREKSEKGR                                       19

SEQ ID NO: 4              moltype = AA  length = 14
FEATURE                   Location/Qualifiers
source                    1..14
                          mol_type = protein
                          organism = Rattus sp.
SEQUENCE: 4
MEESQSKEES NTEG                                            14
```